US00PP21290P3

(12) United States Plant Patent
Meinl

(10) Patent No.: US PP21,290 P3
(45) Date of Patent: Sep. 14, 2010

(54) **VARIETY OF *HYDRANGEA* PLANT NAMED 'HORMEI'**

(50) Latin Name: ***Hydrangea macrophylla* hybrid**
Varietal Denomination: Hormei

(75) Inventor: Katrin Meinl, Dresden (DE)

(73) Assignee: Claus & Torsten Kühne GbR, Dresden (DE)

( * ) Notice: Subject to any disclaimer, the term of this patent is extended or adjusted under 35 U.S.C. 154(b) by 0 days.

(21) Appl. No.: 12/313,824

(22) Filed: Nov. 25, 2008

(65) Prior Publication Data

US 2010/0132083 P1 May 27, 2010

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Upov Plant Variety Database 2009/03 p. 1.*

* cited by examiner

*Primary Examiner*—Annette H Para
(74) *Attorney, Agent, or Firm*—The Webb Law Firm

(57) ABSTRACT

A new and distinct *Hydrangea* plant having pink flowers, strong vigor and good branching.

1 Drawing Sheet

Botanical classification: *Hydrangea macrophylla* hybrid.
Varietal denomination: 'Hormei'.

BACKGROUND OF THE INVENTION

The present invention comprises a new and distinct cultivar of *Hydrangea* plant known by the varietal name 'Hormei'. The new variety was discovered in 2000 in a planned breeding program in Dresden, Germany. The purpose of the breeding program was to develop compact, blue Hydrangeas. The new variety is the result of mixed pollination between nine different genotypes of proprietary *Hydrangea* plants. The new variety was first asexually reproduced in 2000 via propagation by cuttings in Germany. The new variety has been trial and field tested in Germany and has been found to retain its distinctive characteristics and remain true to type through successive propagations.

The following traits distinguish 'Hormei' as a new and distinct cultivar from other *Hydrangea* varieties known to the breeder:

1. Forcing time;
2. Branching;
3. Number of sterile flowers;
4. Vigor; and
5. Stem quality.

'Hormei' is similar to another *Hydrangea* variety, 'Blauling' (unpatented), in color and lacecap. However, 'Hormei' differs from 'Blauling' in forcing time, branching, and sterile flower number.

DESCRIPTION OF THE DRAWING

The accompanying photographic drawing illustrates the new variety, with the color being as nearly true as is possible with color illustrations of this type.

DESCRIPTION OF THE PLANT

Figure 1:
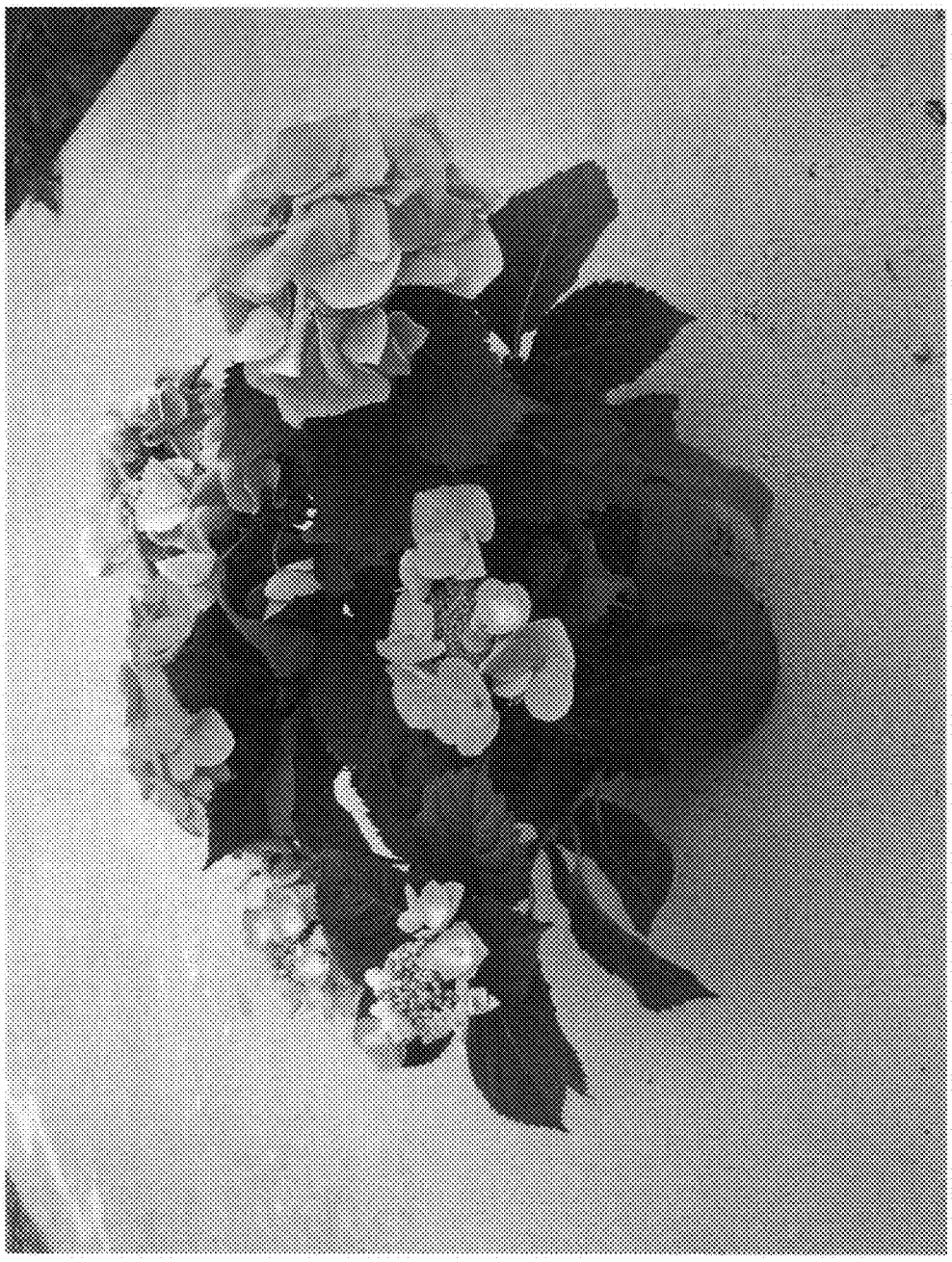
FIG. 1 is photograph of an entire plant of the new variety.

The following detailed description sets forth characteristics of the new cultivar. The plants were grown in 13 cm. pots in peat substrate at a pH of 5.7 and were 10 months past propagation when described. Measurements and color readings of the plants were taken in Dresden, Germany under natural light with a shadow present. Color references are primarily to The R.H.S. Colour Chart of The Royal Horticultural Society of London.

PLANT

*Time to initiate roots.*—About 15 days at 18° C.
*Time to develop roots.*—About 20 days at 18° C.
*Rooting habit.*—Strong and adventitious root system.
*Time to produce a finished flowering plant from a rooted cutting.*—About 40 weeks in a 13 cm. container.
*Form.*—Symmetrical.
*Height (from media surface to top of foliage).*—20.0 cm.
*Height (from media surface to top of flowers).*—26.0 cm.
*Plant diameter.*—45.0 cm.
*Vigor.*—Strong.
*Strength.*—No artificial support needed.
*Branching habit.*—Well-branched.
*Trunk.*—Main trunk length: 1.0 cm. Diameter: 0.8 cm. Color: 199D. Texture: Woody. Pubescence: Absent. Internode length: 1.2 cm.
*Lateral branches.*—Length: Young: 18.0 cm. Mature: 0.5 cm. Diameter: Young: 0.5 cm. Mature: 0.6 cm. Internode length: 3.3 cm. Texture: Smooth with dark lenticels. Pubescence: Absent. Lenticel: Length: 1.0–2.0 mm. Width: 0.5 mm. Shape: Mostly elongated. Color: Young: 144B. Mature: 199D. Lenticel color: 177A.

*Foliage.*—Arrangement: Mostly opposite disposition. Size of leaf: Length: 10.0 cm. Width: 6.0 cm. Shape of leaf (generally): Young: Long and ovate. Mature: Long and ovate. Shape of apex: Cuspidate. Shape of base: Obtuse. Texture: Matte. Aspect: Slightly undulate. Margin type: Serrate. Pubescence: None present. Color: Young leaves: Upper surface: 139A. Lower surface: 137B. Mature leaves: Upper surface: 139A. Lower surface: 137B. Petiole: Shape: U-shaped. Length: 2.5 cm. Diameter: 0.3 cm. Color: 143B. Veins: Venation type: Pinnate. Color: Upper surface: 138A. Lower surface: 138B.

FLOWER

*Natural flowering season.*—July in Dresden, Germany.

*Flower habit.*—Early blooming after 7 weeks of forcing.

*Bud.*—Stage of development when described: At full coloration. Shape of cluster: Round. Diameter of cluster: 4.0 cm. Number of buds per cluster: More than 50. Shape: Fertile: Round. Sterile: Round. Length: Fertile: 0.6 cm. Sterile: 0.2 cm. Width: Fertile: 0.4 cm. Sterile: 0.3 cm.

*Inflorescence.*—Shape: Lacecap. Length: 7.0 cm. Diameter: 15.0 cm. Average number of flowers per inflorescence: Sterile: More than 60. Fertile: More than 6. Average number of inflorescences per plant: 7. Lastingness: Fertile: Two weeks. Sterile: Four weeks.

*Petals.*—Number per flower: 4 to 6. Color: Upper surface: 75C. Lower surface: 75C. Shape: Ovate. Length: 0.5 cm. Width: 0.25 cm. Apex: Pointy. Base: Obtuse. Margin: Entire. Texture: Smooth. Tonality from a distance: Mixed color.

*Sepals.*—Number per flower: 4 to 6. Color: 145C. Shape: Ovate. Length: 0.2 cm. Width: 0.1 cm. Apex: Pointy. Base: Obtuse. Margin: Entire. Texture: Smooth. Fused: Yes. Petaloids: Quantity: 4 to 5. Shape: Round to ovate. Length: 2.0 cm. Width: 1.8 cm. Color: Upper surface: 73A. Lower surface: 73D.

*Pedicels.*—Length: Fertile: 0.7 cm. Sterile: 2.5 cm. Diameter: Fertile: 0.1 mm. Sterile: 0.15 cm. Color: 73D.

*Peduncles.*—Length: 4.0 cm. Diameter: 0.3 cm. Texture: Smooth with dark lenticels. Color: 143D.

*Stamens.*—Number per fertile flower: 7 to 9. Filament: Length: 0.3 cm. Color: 65C. Anthers: Shape: Round to elongated. Length: 0.1 cm. Color: 1D. Pollen: Color: 1D. Amount: Plentiful.

*Pistils.*—Number: 1, divided into 3 parts. Length: 0.1 cm. Style: Length: 0.1 cm. Color: 65C. Stigma (divided into 3 parts): Color: 65D. Diameter: 0.2 cm. Ovaries (inferior): Length: 0.3 cm. Width: 0.2 cm. Color: 1D.

*Fragrance.*—Fresh and "green".

*Disease resistance.*—Tolerant to botrytis and powdery mildew.

*Temperature tolerance.*—Medium, not fully winterhardy flower buds in Germany.

*Drought tolerance.*—Medium.

I claim:

1. A new and distinct variety of *Hydrangea* plant substantially as shown and described herein.

* * * * *

UNITED STATES PATENT AND TRADEMARK OFFICE

CERTIFICATE OF CORRECTION

PATENT NO. : PP21,290 P1
APPLICATION NO. : 12/313824
DATED : September 14, 2010
INVENTOR(S) : Meinl It is certified that error appears in the above-identified patent and that said Letters Patent is hereby corrected as shown below:

Column 4, line 8, "Diameter: Fertile: 0.1 mm." should read -- Diameter: Fertile: 0.1 cm. --

Signed and Sealed this
Twenty-fifth Day of January, 2011

David J. Kappos

David J. Kappos
*Director of the United States Patent and Trademark Office*